(12) United States Patent
Rashidi

(10) Patent No.: US 7,245,955 B2
(45) Date of Patent: Jul. 17, 2007

(54) ELECTROPHYSIOLOGY/ABLATION CATHETER HAVING DEFLECTION ASSEMBLY

(75) Inventor: Rassoll Rashidi, Lakewood, OH (US)

(73) Assignee: St. Jude Medical, Atrial Fibrillation Division, Inc., Maple Grove, MN (US)

( * ) Notice: Subject to any disclaimer, the term of this patent is extended or adjusted under 35 U.S.C. 154(b) by 315 days.

(21) Appl. No.: 10/784,511

(22) Filed: Feb. 23, 2004

(65) Prior Publication Data
US 2005/0187455 A1  Aug. 25, 2005

(51) Int. Cl.
*A61B 5/04* (2006.01)
*A61B 18/14* (2006.01)

(52) U.S. Cl. .................. 600/374; 600/381; 606/41

(58) Field of Classification Search .................. 606/41; 607/99, 113
See application file for complete search history.

(56) References Cited

U.S. PATENT DOCUMENTS

| | | | |
|---|---|---|---|
| 5,383,852 A * | 1/1995 | Stevens-Wright | 604/95.04 |
| 5,552,713 A | 9/1996 | Rashidi | |
| 5,861,024 A | 1/1999 | Rashidi | |
| 6,572,611 B1 * | 6/2003 | Falwell | 606/41 |
| 6,671,533 B2 * | 12/2003 | Chen et al. | 600/374 |
| 7,013,169 B2 * | 3/2006 | Bowe | 600/374 |
| 2002/0065514 A1 | 5/2002 | Rassoll | |
| 2003/0109778 A1 | 6/2003 | Rassoll | |
| 2003/0208198 A1 * | 11/2003 | Hayzelden et al. | 606/41 |

* cited by examiner

*Primary Examiner*—Lee S. Cohen
(74) *Attorney, Agent, or Firm*—Wiley Rein LLP

(57) ABSTRACT

An electrophysiology/ablation catheter assembly includes an elongated flexible casing that received a first catheter deflection assembly. Electrical leads are connected to each electrode on a distal portion of the catheter assembly and extend through the casing for external connection at a proximal end of the catheter assembly. A first actuator is operatively connected to the first catheter deflection assembly and operable upon movement to selectively effect displacement of the distal end. A second catheter deflection assembly is also disposed in the casing. A second actuator is connected adjacent the proximal end of the catheter deflection assembly and operable upon movement to selectively effect lateral displacement of the catheter at a location spaced from the first curved configuration of the distal end.

8 Claims, 2 Drawing Sheets

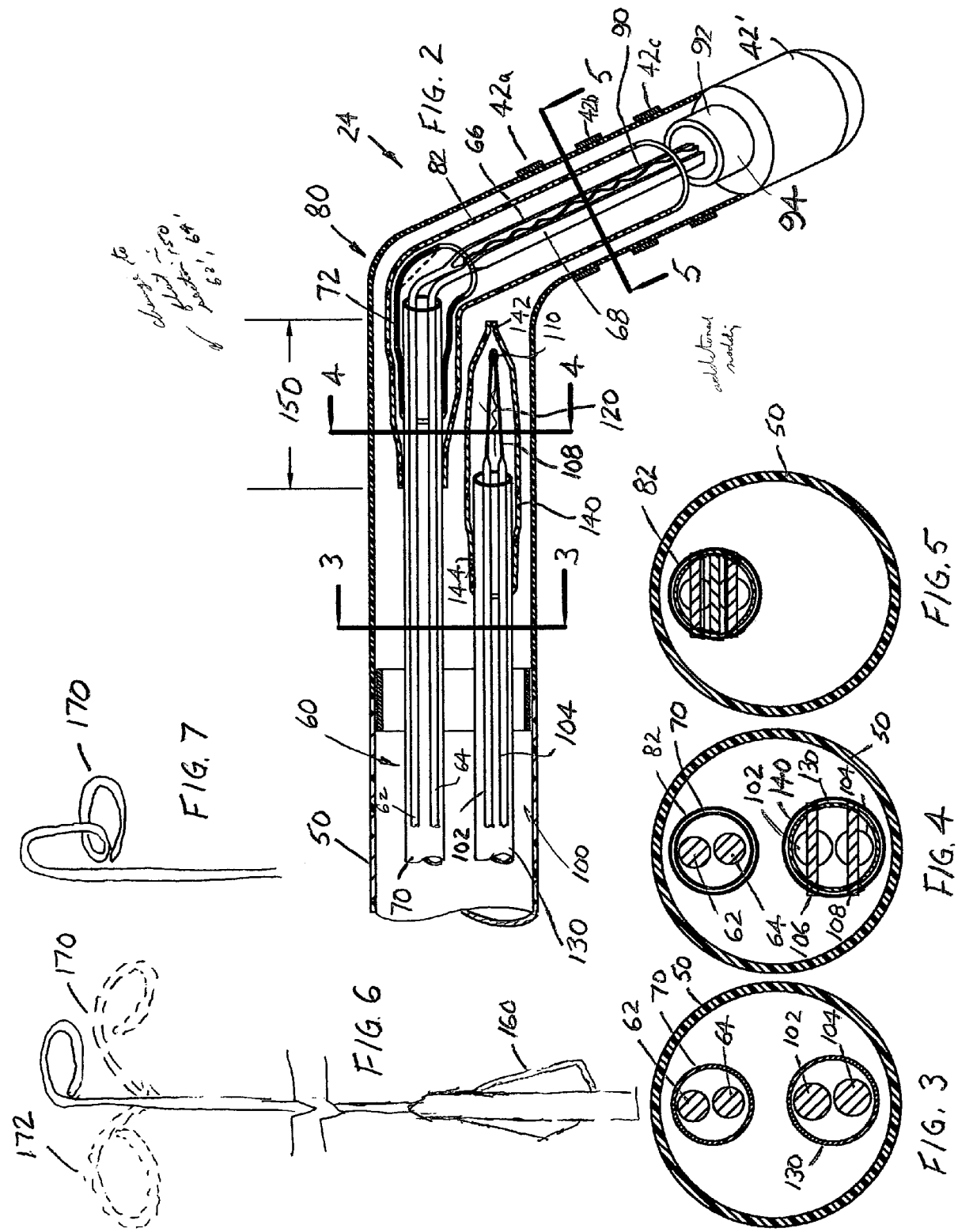

ELECTROPHYSIOLOGY/ABLATION CATHETER HAVING DEFLECTION ASSEMBLY

BACKGROUND OF INVENTION

This application is directed to a catheter assembly, and particularly an electrophysiology/ablation catheter of the type used for diagnostic and therapeutic medical procedures. It finds particular application in minimally invasive cardiac electrophysiology studies such as cardiac diagnostic or ablation procedures in which precise and controlled movement of conductive electrodes provided on a distal portion of the catheter are required.

It is known from commonly owned U.S. Pat. Nos. 5,552,713 and 5,861,024 to provide an electrophysiology/ablation catheter to monitor and record intra-cardiac electrical signals. The details of these patents are expressly incorporated herein by reference. The electrical signals from the heart are conducted through the electrodes to associated monitoring and recording devices. The electrodes can also be used, for example, to deliver energy to the heart either as a stimulus to monitor the heart's response thereto or to deliver energy for ablation procedures if required.

As will be appreciated, these procedures require careful placement and manipulation of the distal portion of the catheter at a particular cardiac cavity. The noted patents describe use of a pair of tension/compression members to orient the axially spaced electrodes in a desired configuration. Generally, and without intending to be a complete synopsis of these patents, a low manual actuation force allows a user to selectively deflect a distal portion of the catheter into a desired form of curvature, for example, into the form of a loop or lariat as also taught in commonly owned U.S. application Ser. No. 726,235, published as 2002-0065514 A1, the disclosure of which is also incorporated herein by reference. The first and second tension/compression members act in concert to provide a desired radius of curvature of the distal portion of the catheter for monitoring purposes. In this manner, the electrodes provided on the distal portion are configured in a desired curvature (for example, a loop) and the assembly can be used for effective cardiac monitoring or mapping and ablation procedures.

The tension/compression members preferably include flattened portions adjacent to what is termed a kinematic junction. That is, as one of the members or wires is placed in tension, the other acts in compression to provide a smooth, controlled deflection of the distal portion. An actuator, such as a delta-shaped (Δ-shaped) actuator shown and described in the '024 patent, is located at the opposite or proximal end portion of the catheter assembly and cooperates with the pair of tension/compression members. By means of a pair of coupled sliders, selective articulation of the actuating member results in deflection of the distal portion of the catheter in one direction or another to form the desired curvature. Thus, the structure is able to curl in a plane substantially perpendicular to the length of the catheter and can deflect or curl in opposite directions depending on the direction of movement of the actuator.

In certain instances, additional bending of the curved (curled) distal portion or loop is required. This would enhance the performance in which the electrophysiology/ablation catheter could be used, and would also provide greater, desired control of its movement. The additional bending feature, however, has been difficult to achieve because of the limited volume or available space within the catheter assembly. This limitation also relates to the available space within the catheter assembly including the catheter handle as a result of the existence of electrical wires extending through the length of the catheter to communicate between the handle at the proximal end of the catheter and the electrodes disposed at the distal end. Moreover, the deflection means or deflection assembly in other prior art arrangements has heretofore been of such size that it limits the use or incorporation of additional components into the catheter assembly.

Accordingly, a need exists for additional, controlled bending feature of the catheter assembly without losing any of the benefits and advantages offered by those shown and described in the commonly owned patents and application.

SUMMARY OF INVENTION

An improved electrophysiology/ablation catheter incorporates first and second actuators that cooperate with independent first and second catheter deflection assemblies to control the bending feature of a distal end portion of the catheter.

Preferably, each catheter deflection assembly includes a pair of tension/compression members extending through the casing.

A first catheter deflection assembly deflects the distal end in a plane substantially normal to a longitudinal extent of the catheter. The second catheter deflection assembly deflects the catheter through a second range of curvature at a location spaced inwardly from the electrodes.

A pre-formed bend is preferably interposed between the first and second catheter deflection assemblies.

Thin walled conduits are provided over flattened portions of the respective tension/compression member pairs to constrain movement of the members in a radial direction upon application of tension and compression forces thereto.

A second actuator is provided at the handle or proximal end of the catheter assembly to independently deflect or curve the distal portion of the catheter via the second catheter deflection assembly as desired.

A second preferred embodiment uses a pre-shaped curvature of the electrodes and an actuator coupled to a deflection assembly that selectively deflects the catheter at a region spaced from the electrodes.

A primary benefit of the invention is the ability to form an additional curvature at the distal portion of the catheter.

Another advantage of the invention resides in the independent actuation of the separate curvature sections.

Still another advantage of the invention resides in the ease with which the assembly may be actuated/operated.

Yet another advantage is found in the incorporation of the additional deflection assembly into a single catheter assembly, which expands the use and capabilities of the catheter assembly.

Still other benefits and advantages of the invention will become apparent to those skilled in the art upon reading and understanding the following detailed description.

BRIEF DESCRIPTION OF DRAWINGS

FIG. 2 is an enlarged view of the distal portion of the catheter of FIG. 1 with selected portions cut-away for ease of illustration.

FIG. 3 is a cross-sectional view taken generally along the lines 3—3 of FIG. 2.

FIG. 4 is a cross-sectional view taken generally along the lines 4—4 of FIG. 2.

FIG. 5 is a view taken generally along the lines 5—5 of FIG. 2.

FIG. 6 is a view of the distal portion of the catheter assembly illustrating a second preferred embodiment of the invention.

FIG. 7 is view similar to FIG. 6 and showing a desired deflection of the distal portion.

DETAILED DESCRIPTION OF THE INVENTION

Figure 1:
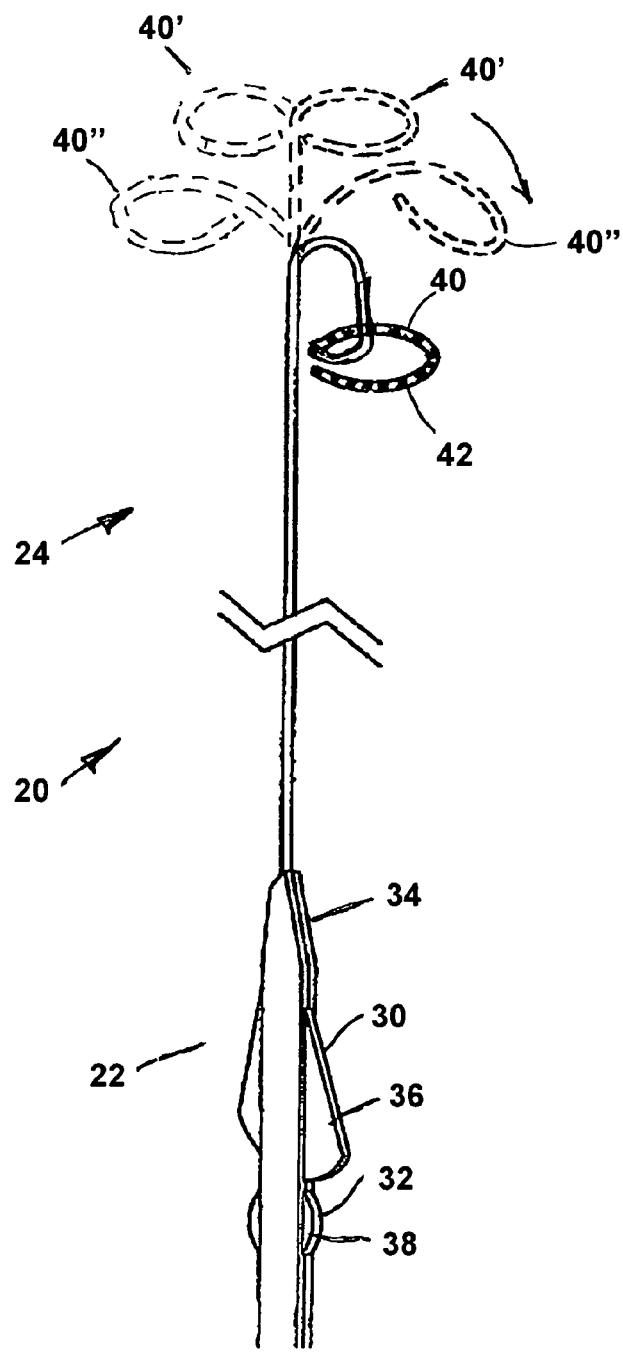
FIG. 1 is a view of the catheter assembly of the present invention.

It will be appreciated that the structure, operation, and advantages offered by a catheter assembly that forms a first curvature or lariat configuration at a distal portion thereof is shown and described in the commonly owned U.S. published application. The structure and operation of the deflection assembly shown and described therein are helpful to an understanding of the present invention. A preferred embodiment of the present invention is shown in FIG. 1 and generally illustrates an electrophysiology/ablation catheter or catheter assembly 20. The catheter assembly includes a proximal portion 22 and a distal portion 24. Particularly, the proximal portion includes independent, axially spaced first and second actuators 30, 32. Each actuator is associated with a separate catheter deflection assembly to be described in greater detail below to achieve different, independent deflection or curvature of the distal portion of the catheter assembly. Moreover, each catheter deflection assembly and associated actuator may be of the type as shown and described in the commonly owned U.S. patents and published application identified above with regard to a preferred form of construction. That is, the catheter assemblies preferably include actuators 36, 38 that are ergonomically shaped and easily operated by a user to cause or actuate deflection of the distal portion of the catheter assembly. Of course, modifications of the precise actuator assemblies can be used without departing from the scope and intent of the present invention, although the illustrated actuator is preferred.

As shown in FIG. 1, the first actuator 30 deflects the distal portion of the assembly into a curved configuration or what has sometimes been referred to as a loop or lariat 40. This lariat is disposed in a direction substantially perpendicular to the longitudinal extent of the catheter assembly and can deflect in opposite directions, i.e., right-handed or left-handed, as shown in FIG. 1 depending on the direction in which the actuator member 36 is moved. Likewise, the extent of curvature is also controlled by the amount of deflection of the actuator 36. It is contemplated that the distal portion of the catheter deflection assembly can form a lariat that extends at least approximately three hundred sixty degrees (360°) so that axially spaced electrodes 42 can be arranged in a substantially circular configuration. The curved configuration can be very tight, or open, depending on the desired end location of the electrodes relative to the body cavity in which it is placed. Selectively opening and closing the lariat also allows desired ablation procedures to be undertaken in addition to mapping of the electrical activity in this region. Thus, as shown in the uppermost phantom representation 40' in FIG. 1, the right-hand lariat configuration is achieved by moving the first actuator 36 in one direction and the mirror image arrangement to the left-hand side is also achieved by moving the actuator member in the opposite direction.

A secondary deflection or bend of the distal portion of the catheter assembly, also referred to herein as "nodding", is provided in response to movement of the second actuator 32. Particularly, movement of the actuator member 38 from the illustrated median position actuates deflection of the distal portion of the catheter assembly, i.e., the distal portion proceeds from that shown in the phantom of 40' (no deflection or nodding), through 40'' (partially nodded) to the final desired position shown in solid line 40 (full deflection or nodding). Likewise, it will be appreciated that a mirror image movement of the distal portion of the catheter assembly can be achieved by moving the second actuator 38 in the opposite direction. Thus, the lariat configuration formed with the first actuator can be moved leftwardly by moving the second actuator member 38 in the opposite direction. Likewise, if only uni-lateral deflection or nodding of the catheter assembly is desired, i.e., nodding in one direction only to either the right or left is desired, or if a greater degree of deflection or nodding in one direction rather than the other is desired, this can be achieved by adjusting the start and finish positions of the push/pull slider members of the actuating assembly. Again, such details are known from the prior patents and published application previously incorporated herein, and when the teachings thereof are applied to the present invention offer a range of alternatives in the dual actuator arrangement of the present invention.

With continued reference to FIG. 1, and additional reference to FIGS. 2–5, the particular structure of the first and second catheter deflection assemblies will be described in greater detail. A catheter housing or casing 50 is preferably a generally tubular conformation. At the distal portion 24 of the catheter assembly, the electrodes 42 are shown in spaced relation. This spaced arrangement includes a distal end electrode 42' which may be slightly different in structure and configuration from the remaining annular electrodes 42a, 42b, and 42c. It will be appreciated by one skilled in the art that the number of electrodes may vary from the particular number illustrated in the accompanying drawings. A first catheter deflection assembly 60 includes first and second tension/compression members or wires 62, 64 operatively associated with the first actuator 36. The wires have a generally circular cross-section throughout a major portion of their length and are preferably formed into non-circular or flattened ribbons 66, 68 in the distal portion for reasons which will become more apparent below. Along a major portion of their length from the proximal end, the tension/compression members 62, 64 are received within a first housing 70, shown as a tubular housing in the preferred embodiment. The first housing defines a first lumen or passage within the outer casing 50. This inner tube 70 is preferably a flexible body, and in the preferred embodiment is made from a polyurethane or polyamide material. A second or outer tube 72 is provided over a distal portion of the tension/compression members. Thus, coaxial guide tubes 70, 72 are provided over the tension/compression members in the region adjacent the preformed bend 80. Moreover, a third or further outer guide tube or sheath 82 extends over the flattened, ribbon-like portions of the tension/compression members, as well as over the first and second housings 70, 72. The third tube extends principally over the flattened or ribbon regions of the tension/compression members and preferably terminates in spaced relation to the end electrode 42' at one end and is reduced in diameter at the other end where it is received over the first guide tube 70 and the reduced diameter end of the second guide tube 72. The longitudinal extent of the guide tubes, however, may vary if desired.

A spacer means or wave-shaped flat spring spacer 90 is received between the flattened, ribbon-like portions 66, 68 of the tension/compression members. The spacer means preferably has a generally rectangular transverse cross-section of substantially the same width as the flattened ribbon portions of the tension/compression members between which it is received. One end of the spacer means is secured between the tension/compression members in a kinematic junction 92. For example, the kinematic junction is formed at the end of the wave-shaped spring and is secured by weldment or brazing with the distal electrode particularly at reduced diameter sleeve 94 thereof. The remainder of the flat spring is free-floating between the tension/compression members and maintains the spacing between the flattened portions of the tension/compression members.

Without repeating all of the structural and functional details of the interconnection between the first actuator and the tension/compression members 62, 64, it will be appreciated that movement of the first actuator 30 in the proximal portion or handle of the catheter assembly results in deflection or curvature of the distal portion. That is, moving the first actuator places one of the members in tension and simultaneously places the other member in compression. In this manner, the distal portion of the catheter assembly is deflected, preferably into the lariat configuration. A smooth transition between the various positions of the catheter distal portion is achieved with this arrangement.

A second catheter deflection assembly 100 is provided in the housing 50 of the catheter assembly. More particularly, the second catheter deflection assembly also preferably includes first and second tension/compression members 102, 104 that include flattened ribbon-like portions 106, 108 at one end thereof and that are preferably secured together at a kinematic junction 110. Also secured in the kinematic junction is one end of spacer means or wave-shaped flat spring spacer member 120 as illustrated in the preferred embodiment. As noted above, the spacer member is secured at one end in the kinematic junction, but is otherwise free-floating between the flattened cross-sectional portions of the tension/compression members.

A first or inner guide tube 130 proceeds over a substantial length of the tension/compression members as they extend through the outer housing 50. The inner guide tube terminates just prior to the ribbon-like portions of the tension/compression members. A second or thin walled tubing 140 is closed at a first end 142 over the kinematic junction 110 and is preferably crimped at a second end 144 to an outer surface of the guide tube 130. Thus, as will be appreciated from FIG. 2, the kinematic junction 110 of the second catheter deflection assembly terminates prior to the preformed bend 80 in the catheter. The tension/compression members 102, 104 are operatively connected with the second actuator 32 in the handle and upon tension in one member and simultaneous compression in the other, the secondary bending or nodding shown in FIG. 1 is achieved. Thus, the lariat configuration formed by the first actuator is progressively advanced into a desired location via the second actuator.

It will be appreciated that the region 150 in the outer casing 50 of the catheter body may be more flexible than the remainder of the casing. This extra flexibility can be achieved by varying material properties or by varying the bending module such as a cross-sectional moment of inertia, of the casing in this region.

As is evident from the cross-sectional configurations of FIGS. 3–5, there is substantial remaining volume within the catheter housing 50 to locate electrical lead wires to the mapping/ablation electrodes provided at the distal portion of the catheter. The tension/compression deflection assembly provides the desired deflection without using all of the available volume or cross-sectional area of the catheter assembly.

In summary, this arrangement is capable of forming an additional curvature of the catheter assembly at its distal portion, preferably below the preformed bend 80 of the catheter. A second pair of tension/compression members 102, 104 are disposed in the main lumen 50 of the catheter. The second pair of tension/compression members have flattened portions 106, 108 at their distal portions. The free ends of the flattened portions are securely welded together to create a second kinematic junction 110. A thin wall conduit means 140 is provided over the flattened portions as well as partially over the round portion of the tension/compression members in order to radially constrain the tension/compression members upon application of tension and compression forces thereto.

An elongated conduit means 130 is sleeved over the entire length of the tension/compression members except over the flattened portions thereof. This elongated conduit 130 radially constrains the tension/compression members upon push/pull actuation of the tension/compression members.

The second actuator 32 is disposed on the catheter handle and is mechanically attached to the proximal ends of the tension/compression members 102, 104 via pair of side-by-side slider means (not shown). As shown in FIG. 1, the first actuator controls desired deflection to form a lariat configuration and the secondary curvature or nodding is formed in response to actuation of the second manual actuator 38 on the catheter handle.

The lariat or loop configuration is formed between the preformed bend and the distal tip of the catheter upon actuating the primary actuator 36 provided on the catheter handle. The secondary bending or nodding takes place at the region 150 as shown in FIG. 2. The secondary bend or nodding region 150 is formed upon actuating the secondary actuator 38 which, in turn, exerts tension in one of the tension/compression members and at the same time applies compression to the second tension/compression member of the pair 102, 104.

The region 150 may be more flexible compared to the remainder of the catheter body that lies between the preformed bend and the proximal end of the catheter. This increased flexibility can be achieved by varying the material properties of the casing 50 or by varying the bending modulus, i.e., the cross-sectional moment of inertia, of this region.

Also contemplated in another preferred embodiment of this invention is use of a pre-shaped lariat configuration. That is, a loop having a plane generally perpendicular to the elongated length of the catheter is provided at a distal portion of the catheter assembly. The catheter casing, proximal to the distal loop, is selectively deflected in a bi-directional manner to cause the nodding feature of this catheter via the steering mechanism 32 provided within the catheter handle. Thus, this alternative arrangement of a preferred catheter assembly has only a single actuator within the catheter handle for causing the nodding action at a region spaced from the preformed lariat configuration. This is illustrated in FIGS. 6 and 7. As shown in FIG. 6, the actuator 160 when advanced in one direction causes bending or nodding in a first direction 170 and when actuated in a second direction provides bending or nodding in a second direction 172, both of which are illustrated in phantom.

The invention has been described with reference to the preferred embodiments. Obviously, modifications and alterations will occur to others upon a reading and understanding of this specification. The invention is intended to include all such modifications and alterations insofar as they come within the scope of the appended claims or the equivalents thereof.

The invention claimed is:

1. An electrophysiology/ablation catheter comprising:
an elongated flexible casing having a proximal end and at least one electrode disposed adjacent a distal end thereof;
an electrical lead connected to each of the electrodes and extending through the casing to adjacent the proximal end thereof, the lead adapted for external connection thereof;
a distal portion of the casing adjacent the distal end being preformed into a curved configuration;
a first catheter deflection assembly disposed in the casing, the first catheter deflection assembly having a pair of tension/compression members extending through the casing; and
a first actuator connected to the pair of tension/compression members adjacent a proximal end of the catheter deflection assembly and operable upon movement to selectively effect lateral displacement of the catheter from a point proximal to the curved configuration of the distal portion.

2. The catheter of claim 1 wherein the pair of tension/compression members each has a generally flattened transverse portion adjacent the distal end.

3. The catheter of claim 2 wherein a remaining portion of each of the pair of tension/compression members is generally circular in cross-section.

4. The catheter of claim 1 further comprising a transversely resilient spacer disposed between the tension/compression members in the distal portion thereof.

5. The catheter of claim 1 wherein the first catheter deflection assembly further comprises an elongated sleeve extending over the tension/compression members.

6. The catheter of claim 1 wherein a distal end of the tension/compression members are secured together to form a kinematic junction.

7. The catheter of claim 1 wherein the first catheter deflection assembly is adapted to effect bi-directional displacement of the catheter distal end.

8. The catheter of claim 1 wherein the first catheter deflection assembly is adapted to effect 180 degree displacement of the catheter distal end.

* * * * *